United States Patent [19]

De Jong et al.

[11] 4,199,513

[45] Apr. 22, 1980

[54] MACROCYCLIC POLYETHER COMPLEXES

[75] Inventors: Feike De Jong; David N. Reinhoudt, both of Amsterdam, Netherlands

[73] Assignee: Shell Oil Company, Houston, Tex.

[21] Appl. No.: 917,124

[22] Filed: Jun. 19, 1978

[30] Foreign Application Priority Data

Jun. 23, 1977 [GB] United Kingdom ............... 26334/77

[51] Int. Cl.$^2$ .......................................... C07D 323/00
[52] U.S. Cl. ................................... 260/338; 549/50
[58] Field of Search ......................................... 260/338

[56] References Cited

PUBLICATIONS

Pedersen, Chem. Abst. vol. 68, 1968, 59555s.
Knipe, J. Chem. Ed., vol. 53, 1976.

*Primary Examiner*—Natalie Trousof
*Assistant Examiner*—Jane T. Fan

[57] ABSTRACT

Novel complexes of macrocyclic polyethers such as 1,4,7,10,13,16-hexaoxacyclooctadecane (18-crown-6) and disulfonates of the formula I

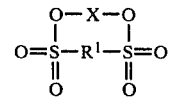

wherein X represents barium or strontium and $R^1$ is an alkylene moiety, optionally substituted with an alkyl group, are described as well as a process for isolating said macrocylic polyethers through formation of said novel complexes. In the isolation process disclosed, a macrocyclic polyether containing solution is contacted with a disulfonate of formula I to afford the polyether-disulfonate complex as a solid suspension in the solution, the suspended complex is separated from the solution and the separated complex is extracted with a solvent for the macrocyclic polyether.

9 Claims, No Drawings

MACROCYCLIC POLYETHER COMPLEXES

BACKGROUND OF THE INVENTION

This invention relates to novel complexes of macrocyclic polyethers and to a process for isolation of these macrocyclic polyethers from mixtures containing them in which the novel complex is advantageously employed to effect separation of the macrocyclic polyether from the mixture.

Macrocyclic polyethers such as 1,4,7,10,13,16-hexaoxacyclooctadecane have a demonstrated ability to solubilize or complex metal cations in both polar and relatively non-polar media, which, in turn, makes them valuable reagents in a variety of synthesis and separation processes. The disclosure of metal cation complexing properties for these macrocyclic polyethers has stimulated considerable technical interest in their preparation as is evidenced by the following synthesis techniques which have been proposed for 1,4,7,10,13,16-hexaoxacyclooctadecane (also referred to hereinafter by its trival name 18-crown-6).

(1) Elimination of hydrogen chloride from 17-chloro-3,6,9,12,15-pentaoxaheptadecanol, followed by ring closure, in the presence of potassium tert-butoxide, see British patent specification No. 1,285,367.

(2) Catalytic oligomerization of ethylene oxide, see U.S. Pat. No. 3,928,386.

(3) Reaction of triethylene glycol with 3,6-dioxa-1,8-dichlorooctane in the presence of potassium hydroxide and 10% aqueous tetrahydrofuran, as described in J.Org.Chem. 39 (1974)2445–2446.

(4) Reaction of triethylene glycol with bis(2-chloroethyl) ether in the presence of potassium hydroxide and tetrahydrofuran without addition of water, as described in "Synthesis" 1976, 515–516.

While the aforementioned methods for preparing 18-crown-6 show a considerable variation in product yield and cost of starting materials, they all illustrate a disadvantage which is prevalent in previous synthetic techniques for preparing such macrocyclic polyethers in that difficult and costly procedures are required to isolate the product polyethers from the reaction mixture.

The technique disclosed for isolating 18-crown-6 from the reaction mixture obtained by processes (1) and (2) above involves chromatographic separation on acid-washed alumina or silica and elution with readily volatile hydrocarbons. This isolation procedure is not particularly attractive from a commercial standpoint because the adsorption capacities of alumina or silica for the 18-crown-6 are rather low and the used alumina or silica must be regenerated or discarded and replaced by fresh alumina or silica.

In the reference processes (3) and (4) above, potassium chloride and tetrahydrofuran are removed from the reaction mixtures and the resulting product is distilled to afford a crude 18-crown-6 overhead product. Subsequently the distilled 18-crown-6 is mixed with acetonitrile and the mixture obtained is cooled to a very low temperature, e.g., −45° C., to precipitate the 18-crown-6-acetonitrile complex which forms on addition of the acetonitrile. The precipitated complex is then filtered off and the acetonitrile is evaporated from the filtered complex at sub-atmospheric pressure with gentle heating. In the reference process (3), the finished 18-crown-6 is obtained by crystallization from the residue while in reference process (4) the residue is distilled to obtain the 18-crown-6 as a distillate. One disadvantage of using acetonitrile in accordance with reference processes (3) and (4) for isolation of the 18-crown-6 is high solubility of 18-crown-6-acetonitrile complex in acetonitrile at ambient temperature. Because of this high solubility, very low temperatures must be used to precipitate the complex from the excess acetonitrile and even then the complexed 18-crown-6 is obtained in rather low yield. A further disadvantage of reference processes (3) and (4) above is that they both include at least one step wherein the 18-crown-6 is distilled overhead, and therefore, additional measures must be taken to avoid the occurrence of powerful and destructive explosions which are known to occur during the distillation of 18-crown-6, see "Chemical and Engineering News," Sept. 6, 1976, page 5 and Dec. 13, 1976, page 5.

From the foregoing, it is apparent that considerable advantage would be obtained if a simple and cost effective means could be found for isolating macrocyclic polyethers from reaction mixtures which avoids the commercial impracticalities and potential hazards associated with previous separation techniques.

SUMMARY OF THE INVENTION

It has now been found that disulfonates of the general formula I

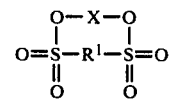

wherein x represents barium or strontium and $R^1$; is an alkylene moiety optionally substituted with an alkyl group, will form novel complexes with macrocyclic polyethers which are compatible with barium or strontium ions. The terms "compatible" as used herein to describe and define suitable macrocyclic polyethers means that the size of the hole in the polyether ring must be sufficient to accomodate the diameter of the barium or strontium ion represented by X in formula I above. The novel disulfonate-polyether complexes of the invention are of special advantage in that they provide a means by which the polyethers can be separated in high yield and purity from mixtures containing them without the need for a potentially hazardous distillation step where the polyether is taken as the distillate. Accordingly, the present invention also provides a process for the isolation of a macrocyclic polyether compatible with a barium or strontium ion from a solution containing said polyether which comprises contacting the solution with a disulfonate of formula I above to form a solid complex of the disulfonate and the macrocyclic polyether, separating the solid complex from the mixture containing the complex and extracting the separated complex with a solvent for the macrocyclic polyether.

DESCRIPTION OF THE PREFERRED EMBODIMENTS

The disulfonate reactants which are suitable for forming the complexes in accordance with the invention include those wherein the alkylene moiety represented by $R^1$ in formula I above has fewer than ten carbon atoms and preferably less than six carbon atoms. In this regard $R^1$ groups having less than three carbon atoms are most preferred. The group $R^1$ may be derived from an alkane by removal of two hydrogen atoms from one carbon atom or of one hydrogen atom from two carbon atoms. Examples of groups $R^1$ are methylene, ethylidene, isopropylidene, dimethylene, trimethylene, tetramethylene and propylene groups. Among the groups $R^1$ having fewer than three carbon atoms the groups —$(CH_2)_n$—, n being an integer of less than 3, are preferred, i.e. methylene and dimethylene groups. Methylene groups are most preferred. The disulfonate of formula I may be water-free or may contain water of crystallization.

The macrocyclic polyether present in the novel complexes should be compatible with a barium and/or a strontium ion, that is the metal ion and the macrocyclic polyether must be stereochemically compatible with regard to the size of the hole in the polyether ring and the diameter of the ion. Hence, the hole in the polyether ring should be capable of accommodating a barium or a strontium ion. The closer the fit between the diameter of the ion and the size of the hole, the more stable the complex will be. Accordingly, preferred macrocyclic polyethers are those consisting of 4 to 10

$$-O-Y- \quad (II)$$

units where Y represents the group

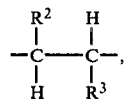

(III)

each of $R^2$ and $R^3$ representing a hydrogen atom or an alkyl group having from one to four carbon atoms. To reduce steric hindrance methyl and ethyl groups are preferred among the alkyl groups which $R^2$ and $R^3$ may represent in formula III. Most preferably, both $R^2$ and $R^3$ represent a hydrogen atom. Preferred complexes are those between barium methanedisulfonate and 1,4,7,10,13,16-hexaoxacyclooctadecane, between barium methanedisulfonate and 1,4,7,10,13,16-hexaoxacyclooctadecane, between barium methanedisulfonate and 1,4,7,10,13-pentaoxacyclopentadecane, between barium 1,2-ethanedisulfonate and 1,4,7,10,13,16-hexaoxacyclooctadecane, and between strontium methanedisulfonate and 1,4,7,10,13,16-hexaoxacyclooctadecane.

Another preferred group of macrocyclic polyethers consists of compound in which the polyether ring in the macrocyclic polyether contains 4 to 10 oxygen atoms and in which (a) each oxygen atom of the polyether ring is separated from the next oxygen atom by two carbon atoms, (b) at least one pair of vicinal carbon atoms of the polyether ring also forms part of an aromatic ring or of a ring obtained by saturation of such as aromatic ring, and (c) each of the carbon atoms of the polyether ring only forming part of the polyether ring is bonded to (1) a hydrogen atom and (2) a hydrogen atom or an alkyl group having from one to four carbon atoms.

The aromatic ring present in the macrocyclic polyether may be a carbocyclic or a hetero-aromatic ring. The preferred carbocylic aromatic ring is the o-phenylene ring. The carbocyclic aromatic rings may be fused, as is the case in, for example, 1,2- and 2,3-naphthylene groups and 1,2- and 2,3-anthrylene groups. Hetero-aromatic rings are derived from hetero-aromatic compounds which are defined as in Kirk-Othmer, "Encyclopedia of Chemical Technology," Second Edition, Volume 2 (1963), page 702: such as those obtained by replacement of one or more carbon atoms of a carbocyclic aromatic compound by a hetero-atom— for example pyridine, pyrimidine, pyrazine, quinoline and isoquinoline—and also include those heterocyclic compounds having five-membered rings which show aromatic characteristics and are mentioned on page 703 of the said volume, for example thiophene, pyrrole, furan, indole and benzothiophene. Examples of hetero-aromatic rings are 2,3-furylene, 2,3-thienylene, 3,4-furylene and 3,4-thienylene rings. The aromatic ring or rings and the rings obtained by saturation of such aromatic rings may carry substituents, for example halogen atoms or alkyl, nitro or cyano groups.

Preferably only one pair of vicinal carbon atoms of the polyether ring also forms part of an aromatic ring or of a ring obtained by saturation of such an aromatic ring. The preferred ring obtained by saturation of an aromatic ring is the 1,2-cyclohexylene ring. Methyl and ethyl groups are preferred among the alkyl groups bound to the carbon atoms of the polyether ring only forming part of the polyether ring. Preferably, each of the latter carbon atoms is bonded to two hydrogen atoms. Preferred complexes are those between barium methanedisulfonate and 2,3-benzo-1,4,7,10,13,16-hexaoxacyclooctadeca-2-ene, between barium methanedisulfonate and 2,3-benzo-1,4,7,10,13,16,19-heptaoxacycloheneicosa-2-ene and between barium methanedisulfonate and 2,5,8,15,18,21-hexaoxatricyclo [20.4.0.0$^{9,14}$]-hexacosane.

In the process according to the invention, the aforedefined disulfonate-macrocyclic polyether complexes are advantageously employed to isolate the polyethers from mixtures containing them. With this process, the macrocyclic polyethers can be obtained in high yield and need not be distilled thereby avoiding the risk of explosions encountered in previous separation processes. Moreover, the solubility of the complex is such that the use of very low temperatures such as those indicated for the prior art processes employing acetonitrile as the complexing agent are not necessary for effective separation of the complex. In fact, the disulfonate reactants in the process of the invention appear to be rather unique in their ability to form solid complexes with compatible polyethers. Specifically, it has been found that replacement of the disulfonate of formula I with a variety of reagents including potassium hexafluorophosphate, barium acetate, barium ethansulfonate, barium p-toluenesulfonate barium succinate and barium 2-methylene-1,3-propanedisulfonate, did not form precipitates in the process according to the invention with mixtures containing 18-crown-6.

The complex formed between a disulfonate of formula I and a compatible macrocyclic polyether contains one molecule of the disulfonate per molecule of macrocyclic polyether. Accordingly, the starting solution containing the macrocyclic polyether is preferably contacted with the disulfonate of formula I using a molar ratio of disulfonate to macrocyclic polyether of at least 1. The reaction mixture formed by contacting the starting solution with such a disulfonate contains as solid materials the complex and any stoichiometric excess of disulfonate. To reduce the excess of disulfonate in the reaction mixture the molar ratio of disulfonate to macrocyclic polyether is preferably not higher than 2. Molar ratios of disulfonate to macrocyclic polyether high than 2, for example up to 5, may be used, if desired, but usually will not be of further advantage. Thus if a molar ratio of disulfonate to macrocyclic polyether of less than 1 gives a complex containing only a very small amount of noncomplexed disulfonate, if any is present at all. In view of these considerations this molar ratio is preferably near to 1.0, for example between 1.0 and 1.1.

The solution containing the macrocyclic polyether may be contacted with the disulfonate of formula I by adding the disulfonate to the solution and stirring the suspension thus formed for, example, 0.5 to 10 hours, to form the solid complex. The macrocyclic polyether present in the mixture obtained upon this reaction partly resides in the complex and the balance is dissolved noncomplexed in the solution obtained. The proportion of the macrocyclic polyether residing in the complex is particularly high, for example more than 97%, when the macrocyclic polyether is 18-crown-6. This proportion is considerably higher than in the case of the 18-crown-6-acetonitrile complex; hence, the 18-crown-6 can be isolated in a correspondingly higher yield. Furthermore, the macrocyclic polyether need not be reacted with the disulfonate of formula I at a very low temperature. The solution containing the macrocyclic polyether is preferably contacted with the disulfonate at a temperature in the range of from $-30°$ C. to $+50°$ C. and particularly in the range of from 15° C. to 30° C. Ambient temperature is very suitable.

A wide variety of solvents may be present in the starting solution containing the macrocyclic polyether to be isolated. Very suitable solvents are alkanols, nitroalkanes, dialkyl sulphoxides, dialkyl ketones, alkanenitriles and dialkyl ethers; all of these solvents preferably have fewer than six carbon atoms per molecule. Particularly preferred are methanol, nitromethane, dimethyl sulfoxide, acetone and acetonitrile. Other examples of suitable solvents are tetrahydrothiophene 1,1-dioxide and N-methylpyrrolidone.

The macrocyclic polyether in the starting mixture may have been formed by any known process. Very good results have been obtained with 18-crown-6 formed by reacting tetraethylene glycol with a bis(2-haloethyl) ether, halo representing chloro, bromo or iodo, in the presence of an alkali metal hydroxide, as described in "Synthesis" 1976, 515–516. If desired, alkali metal halide formed may be removed from the reaction mixture obtained, leaving the 18-crown-6-containing starting solution.

The disulfonates of formula I are selective in that, when contacted with a mixture containing 18-crown-6 and one or more other compatible macrocyclic polyethers, they preferentially form complexes with 18-crown-6. Hence, 18-crown-6-containing starting mixtures containing one of more other compatible macrocyclic polyethers are very suitable starting materials, particularly, those obtained by catalytic oligomerization of ethylene oxide, as described in U.S. Pat. No. 3,928,386.

The suspended complex can easily be separated from the solution obtained, for example by filtration, centrifugation or decantation.

As the solid complexes between a disulfonate of formula I and a macrocyclic polyether in the presence of a solvent for the macrocyclic polyether are in equilibrium with the solid disulfonate and dissolved macrocyclic polyether, the complex can simply be extracted with such a solvent, thus giving a solution of the macrocyclic polyether and leaving the solid disulfonate. The temperature at which this extraction is carried out is not critical and is preferably in the range of from 50° C. to 125° C. Suitable solvents are, for example, nitromethane, acetonitrile and tetrahydrofuran. Evaporation of the solvent from the solution of the macrocyclic polyether at subatmospheric pressure leaves the macrocyclic polyether. This macrocyclic polyether is very pure and need not be distilled. When nitromethane is used as the solvent and 18-crown-6 as the macrocyclic polyether, a residue of the 18-crown-6-nitromethane complex is first formed. The latter complex is described in our copending patent application Ser. No. 917,125 filed of even date (common assignee). When acetonitrile is used as the solvent and 18-crown-6 as the macrocyclic polyether, a residue of the 18-crown-6-acetonitrile complex is first formed. Upon further heating the 18-crown-6-nitromethane complex is decomposed into 18-crown-6 and nitromethane and the 18-crown-6-acetonitrile complex into 18-crown-6 and acetonitrile. The disulfonate of formula I, left after the extraction with the solvent for the macrocyclic polyether, may be reused for complexing further quantities of compatible macrocyclic polyether.

The invention will now be illustrated by reference to the following Examples.

The barium methanedisulfonate used was water-free.

EXAMPLE I

A suspension obtained by addition of barium methanedisulfonate (1 mmol) to a 0.1 M solution (20 ml) of 18-crown-6 in methanol was stirred for six hours at 20° C., the molar ratio of barium methanedisulfonate to 18-crown-6 being 0.5. Then, analysis by NMR spectroscopy of the filtrate obtained by filtration showed that the barium methanedisulfonate had removed 1 mmol of the 18-crown-6. Hence, the filtered material was an equimolar complex between barium methanedisulfonate and 18-crown-6. An elemental analysis of this complex gave the results presented in Table I. These results are compared with the percentages calculated for the equimolar complex.

TABLE I

|  | Found, %w | Calculated, %w |
|---|---|---|
| Carbon | 26.1 | 27.1 |
| Hydrogen | 4.9 | 4.5 |
| Barium | 23.3 | 23.9 |

EXAMPLES II–VI AND COMPARATIVE EXPERIMENT A

A suspension obtained by addition of barium methanedisulfonate (1.5 mmol) to a 0.1 M solution (10 ml) of a macrocyclic polyether in methanol was stirred for one hour at 25° C. Then, analysis by NMR spectroscopy of the filtrate obtained by filtration of the reaction mixture gave the percentage of macrocyclic polyether removed from the starting solution, presented in Table II. Six macrocyclic polyethers were tested in this manner; their structural formulas are shown in Table II along with the results of the tests. Specifically, Table II shows that barium methanedisulfonate removed macrocyclic polyethers 1 to 5 and hardly remove macrocyclic polyether 6, if at all. Hence, macrocyclic polyethers 1 to 5 are compatible and macrocyclic polyether 6 is not compatible with barium ions.

TABLE II

| Example | Macrocyclic Polyether (Name and Structure) | % Removed |
|---|---|---|
| II | 1,4,7,10,13,16-hexaoxacyclooctadecane | 98 |
| III | 2,3-benzo-1,4,7,10,13,16-hexaoxacyclooctadeca-2-ene | 93 |
| IV | 1,4,7,10,13-pentaoxacyclopentadecane | 73 |
| V | 2,3-benzo-1,4,7,10,13,16,19-heptaoxacycloheneicosa-2-ene | 25 |
| VI | 2,5,8,15,18,21-hexaoxatricyclo[20.4.0.0$^{9,14}$]hexacosane | 24 |
| Comparative Experiment A | 3,5-benzo-1,7,10,13,16-pentaoxacyclooctadeca-3-ene | less than 5 |

EXAMPLES VII AND VIII AND COMPARATIVE EXPERIMENTS B-I

Ten experiments were carried out as described in Example II, the difference being that the barium methanedisulfonate was replaced by 1.5 mmol of another salt. Table III states the ten salts used and presents the results.

TABLE III

| Example | Salt | % of 18-crown-6 removed |
|---|---|---|
| VII | barium 1,2-ethanedisulfonate | 90 |
| VIII | strontium methanedisulfonate | 80 |
| Comparative Experiment | | |
| B | calcium methanedisulfonate | 0 |
| C | barium malonate | 0 |
| D | barium ethanesulfonate | 0 |
| E | barium acetate | 0 |
| F | barium p-toluenesulfonate | 0 |
| G | barium succinate | 0 |
| H | potassium hexafluorophosphate | 0 |
| I | barium 2-methylene-1,3-propanedisulfonate | |

EXAMPLE IX-XV

A suspension obtained by addition of barium methanedisulfonate (0.3 mmol) to a 0.1 M solution (2 ml) of 18-crown-6 was stirred for four hours at 20° C. Then, analysis by NMR spectroscopy of the filtrate obtained by filtration of the reaction mixture gave the percentage of 18-crown-6 removed from the starting solution. Seven solvents were tested in this manner. Table IV presents the results.

TABLE IV

| Example | Solvent | % 18-crown-6 removed | Example | Solvent | % 18-crown-6 removed |
|---|---|---|---|---|---|
| | | | XII | acetonitrile | 71 |
| | | | XIII | diethyl ether | 48 |
| IX | nitromethane | 92 | XIV | bromobenzene | 42 |
| X | dimethyl sulfoxide | 88 | XV | toluene | 26 |
| XI | acetone | 15 | | | |

EXAMPLE XVI

A suspension obtained by addition of barium methanedisulfonate (0.104 mmol) to a solution in methanol 1.5 ml of 0.10 mmol of 18-crown-6 and 0.10 mmol of 1,4,7,10,13-pentaoxacyclopentadecane (macrocyclic polyether of Example IV) was stirred for six hours at 20° C. The molar ratio of the macrocyclic polyether of Example IV to 18-crown-6 in the filtrate obtained by filtration of the reaction mixture was 7:1, indicating that 18-crown-5 is preferentially complexed.

EXAMPLES XVII–XIX

A suspension obtained by addition of a solvent (20 ml) to the 18-crown-6-barium methanedisulfonate complex (0.35 mmol) was heated under reflux for 16 hours. Then the suspended solid material was filtered off at reflux temperature and the filtrate obtained was boiled down at a pressure of 1.9 Pa, leaving a residue of 18-corwn-6. Three solvents were tested in this manner. Table V presents the yield of 18-crown-6, calculated on 18-crown-6 in the starting complex.

TABLE V

| Example | Solvent | Yield of 18-crown-6, % |
|---|---|---|
| XVII | tetrahydrofuran | 20 |
| XVIII | acetonitrile | 30 |
| XIX | nitromethane | 27 |

EXAMPLES XX AND XXI

The 18-crown-6-barium methanedisulphonate complex (1 mmol) was continuously extracted for 16 hours in a Soxhlet apparatus. At the end of this period the percentage of the 18-crown-6 extracted from the complex was determined. Two solvents were tested. Table VI presents the results.

TABLE VI

| Example | solvent | % 18-crown-6 extracted |
|---|---|---|
| XX | Acetonitrile | 76 |
| XXI | Nitromethane | 92 |

PREPARATION OF CRUDE 18-CROWN-6

A 3 l three-necked round-bottomed flask, fitted with a mechanical stirrer, a reflux condenser and a 250-ml dropping funnel was charged with potassium hydroxide pellets (416 g. containing 6.3 mol KOH), tetraethylene glycol (1.25 mol) and tetrahydrofuran (1000 ml). The reaction vessel was placed in a heating mantle and gently heated. After 15 minutes a solution of bis(2-chloroethyl) ether (3.125 mol) in tetrahydrofuran (150 ml) was added in one stream from the dropping funnel to the vigorously stirred reactants. The reaction mixture was then heated under reflux, with stirring for 18 hours. Subsequently, the reaction mixture was cooled and boiled down under a pressure of 1.9 kPa to give a brown slurry to which dichloromethane (750 ml) was added. The resulting suspension of potassium chloride was filtered and the potassium chloride filtered off was washed with dichloromethane (100 ml). The combined filtrate and washings were dried over anhydrous magnesium sulphate and the solvent was evaporated at a pressure of 1.9 kPa to give a residue of crude 18-crown-6 (396 g) containing 0.531 mol of 18-crown-6 (yield 42.5%, calculated on starting tetraethylene glycol), potassium chloride and at least eight other compounds among which 1,4,7,10,13,16,19,22,25,28,31,34-dodecaoxacyclohexatriacontane, hexaethylene glycol and unreacted tetraethylene glycol. The crude 18-crown-6 was used as described hereinafter.

COMPARATIVE EXPERIMENT J

Crude 18-crown-6 (39.6 g), prepared as described above, was distilled at a pressure of 20 Pa to give a distillate (21.3 g) boiling at 140°–210° C. This distillate was mixed with acetonitrile (53 ml) at 20° C. and the mixture formed was cooled to −45° C. The resultant 18-crown-6-acetonitrile complex was filtered off and subjected to distillation at a pressure of 2 Pa to give a distillate of 18-crown-6 in a yield of 25% calculated on starting tetraethylene glycol, or 59% calculated on 18-crown-6 in the crude 18-crown-6.

COMPARATIVE EXPERIMENT K

Crude 18-crown-6 (3.021 g), prepared as described above, was dissolved in acetonitrile (4 ml), the solution formed was cooled to −20° C. and the 18-crown-6-acetonitrile complex was filtered off. The complex was kept for 30 minutes at 70° C. and a pressure of 13 Pa, leaving 18-crown-6 in a yield of 27% calculated on starting tetraethylene glycol, or 63% calculated on 18-crown-6 in the crude 18-crown-6.

EXAMPLE XXII

Crude 18-crown-6 (0.991 g), prepared as described above, was dissolved in methanol (38 ml), barium methanedisulphonate (5.7 mmol) was added to the solution obtained and the suspension formed was stirred for six hours at 20° C. Then, the suspended material (1.82 g) was filtered off and extracted with nitromethane (180 ml) in a Soxhlet apparatus. The extract phase obtained was boiled down at a pressure of 1.6 kPa to yield a crystalline residue of the 18-crown-6-nitromethane complex. The complex was kept for 30 minutes at 70° C. and a pressure of 13 Pa, leaving 18-crown-6 in a yield of 35%, calculated on starting tetraethylene glycol, or 79%, calculated on 18-crown-6 in the crude 18-crown-6.

EXAMPLE XXIII

A solution of crude 18-crown-6 (1.202 g) prepared as described above in methanol (30 ml) was cooled to −25° C. Barium methane-disulphonate (6.75 mmol) was added to the cooled solution and the suspension formed was stirred for five hours at −25° C. Then, the suspended material (2.26 g) was filtered off and extracted with nitromethane (200 ml) in a Soxhlet apparatus. The extract phase obtained was boiled down at a pressure of 1.6 kPa to yield a crystalline residue of the 18-crown-6-nitromethane complex. The complex was kept for 30 minutes at 70° C. and a pressure of 13 Pa, leaving 18-crown-6 in a yield of 30% calculated on starting tetraethylene gyocl, or 72% calculated on 18-crown-6 in the crude 18-crown-6.

What is claimed is:

1. A chemical complex formed between a macrocyclic polyether compatible with barium or strontium ions and a disulfonate of the formula

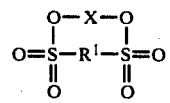

wherein X represents a barium or strontium atom and $R^1$ is from 1 to 10 carbon atoms and is an alkylene moiety, optionally substituted with an alkyl group; said macrocyclic polyether being selected from that class consisting of:

(A) macrocyclic polyethers consisting of 4 to 10

—O—Y— units where Y represents the group

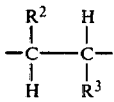

each of $R^2$ and $R^3$ representing a hydrogen atom or an alkyl group having from one to four carbon atoms and (B) macrocyclic polyethers in which the polyether ring contains 4 to 10 oxygen atoms and in which
(a) each oxygen atom of the polyether ring is separated from the next oxygen atom by two carbon atoms,
(b) at least one pair of vicinal carbon atoms of the polyether ring also formed part of a carbocyclic aromatic ring selected from the class consisting of o-phenylene, 1,2-naphthylene, 2,3-naphthylene, 1,2-anthrylene and 2,3-anthrylene or a ring obtained by saturation of said aromatic ring, and
(c) each of the carbon atoms of the polyether ring only forming part of the polyether ring is bonded to (1) a hydrogen atom and (2) a hydrogen atom or an alkyl group having from one to four carbon atoms.

2. The complex as claimed in claim 1, in which the group $R^1$ has fewer than six carbon atoms.

3. The complex as claimed in claim 2, in which the group $R^1$ has fewer than three carbon atoms.

4. The complex as claimed in claim 1, in which the macrocyclic polyether consists of 4 to 10

—O—Y— units, where Y represents the group

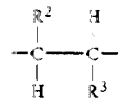

each of $R^2$ and $R^3$ representing a hydrogen atom or an alkyl group having from one to four carbon atoms.

5. The complex as claimed in claim 1, in which $R^2$ and $R^3$ both represent a hydrogen atom.

6. The complex formed between barium methanedisulfonate and 1,4,7,10,13,16-hexaoxacyclooctadecane.

7. The complex formed between barium 1,2-ethanedisulfonate and 1,4,7,10,13,16-hexaoxacyclooctadecane.

8. The complex formed between strontium methanedisulfonate and 1,4,7,10,13,16-hexaoxacyclooctadecane.

9. The complex formed between barium methanedisulfonate and 1,4,7,10,13-pentaoxacyclopentadecane.

* * * * *